United States Patent [19]

Dorman

[11] 4,149,227

[45] Apr. 10, 1979

[54] REFLECTOR

[75] Inventor: William H. Dorman, Corning, N.Y.

[73] Assignee: Corning Glass Works, Corning, N.Y.

[21] Appl. No.: 808,170

[22] Filed: Jun. 20, 1977

[51] Int. Cl.[2] .......................... F21V 7/00; A61B 1/06

[52] U.S. Cl. .................................. 362/297; 362/348; 362/804

[58] Field of Search ............... 362/257, 296, 297, 346, 362/347, 348, 350, 804; 350/288, 292, 293, 294, 295

[56] References Cited

U.S. PATENT DOCUMENTS

| | | | |
|---|---|---|---|
| 2,437,516 | 3/1948 | Greppin | 362/348 |
| 3,191,023 | 6/1965 | Sullivan et al. | 362/220 |
| 3,449,561 | 6/1969 | Basil et al. | 350/293 |
| 3,511,983 | 5/1970 | Dorman | 362/297 |
| 3,666,939 | 5/1972 | Ota | 362/297 |

*Primary Examiner*—J D Miller
*Assistant Examiner*—Peter S. Wong
*Attorney, Agent, or Firm*—John P. DeLuca; Burton R. Turner; Clarence R. Patty, Jr.

[57] ABSTRACT

A reflector useful in dental surgical lighting systems has been developed, which reflector is derived from at least one base elipsoid surface which has been divided into sections, each section being rotated outward so as to provide the cumulative effect of several elipsoidal segments to produce a beam pattern of desired width.

25 Claims, 15 Drawing Figures

$\emptyset$ = LPQ, $\emptyset_2$ = RPJ, $\emptyset_3$ = TPU

θ = OFL = QFR = JFT

REFLECTOR

BACKGROUND OF THE INVENTION

This invention relates to lighting devices of the type generally used by dentists for illuminating the oral cavity of a patient during the performance of dental or surgical procedures. Such devices are generally constructed with reflectors in the form of portions of elipsoids of revolution, i.e., surfaces formed by revolving an elipse about a major axis. A light source is located transverse to the axis of the elipsoid at one focus thereof, while the device is oriented such that the oral cavity of the patient is in the vicinity of the conjugate focus. It has been customary to employ in such devices, light sources having filaments elongated in directions transverse to the major axis of the reflector. Due to the transverse extent of the filament, a light pattern of somewhat elongated width has been formed in the area of the conjugate focus. It has been found however that it is necessary to modify the shape of the reflector surface and the filament geometry in order to enhance the pattern of the beam.

Modification of the shape and geometry of the filament has provided helpful but is not a complete solution to the requirements for producing intense pattern of light in the vicinity of the desired zone of illumination, i.e., the patient's oral cavity.

Modification of the reflector surface has also proved useful, but stray light rays commonly known as "fishtails" have been produced by the modified shape of the reflector. One of the reasons for the production of such fishtails is that the basic reflector surface has been modified so that it does not in all respects behave as a mathematical model. For example in a true elipsoid, a ray leaving the primary focus and striking any surface of the elipsoid will be reflected through the conjugate focus. Since no reflector surface is perfect and since no ideal point source is available, the pattern about the conjugate focus will be somewhat distorted. Generally however, the pattern will be concentrated. By elongating the filament along the various axes of the elipsoidal surface, or by distorting the shape of the elipsoid itself, variations in the width, height, and depth of the light pattern at the conjugate focus can be produced. These efforts however have not been accurately predictable and they are based many times upon approximations and emperical trials.

The present invention provides for a modification of the reflector surface such that a predictable pattern will be produced which pattern can be changed by variations in the parameters which have been developed in connection with the present invention.

SUMMARY OF THE INVENTION

According to the invention, a dental lighting device of the conventional type is provided with a transversely oriented filament light source. In order to form a light pattern of useful dimensions at the conjugate focus of the reflector, the basic elipsoidal configuration of the reflector is modified by the controlled rotation of portions of at least one base elipsoidal surface around one primary focus so that the conjugate focus is displaced in a transverse direction relative to the major axis. A portion of the elipsoidal surface so produced forms one segment of a compound elipsoidal surface of the reflector of the present invention. The base elipsoidal surface may again be rotated in space to move the conjugate focus to a different point transverse with the major axis. A portion of the base elipsoidal surface so produced is aligned with and placed adjacent to the first mentioned rotated elipsoidal surface segment. This process is continued until a beam pattern of the desired width is produced.

The surface produced by principles disclosed herein may be continuous, i.e., a single moulded structure, containing definite regions having predictable and accurately reproducible properties.

DESCRIPTION OF THE PREFERRED EMBODIMENT

Figure 1:
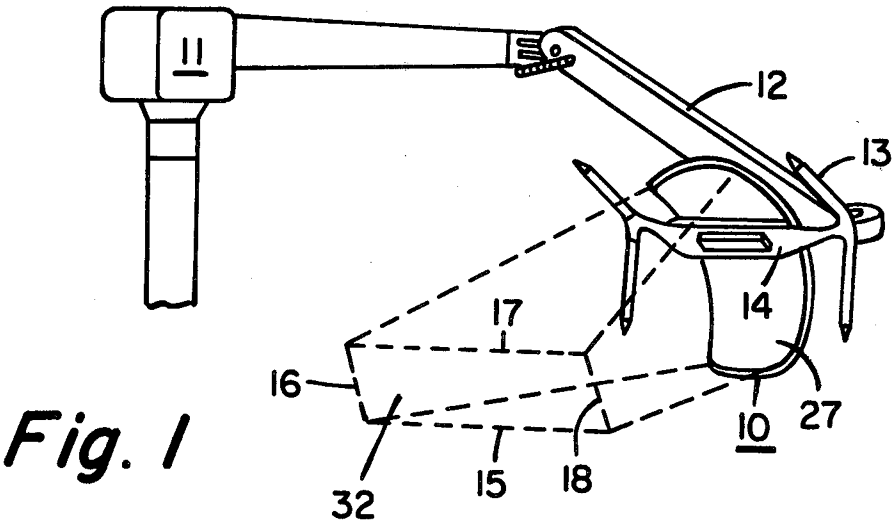
FIG. 1 is a schematic representation of a lighting fixture showing the environmental application of the reflector of the present invention.

In a preferred embodiment, the lighting device of the present invention comprises a glass reflector 10 in the form of portions of at least one base elipsoid revolution. The reflector 10 illustrated in FIG. 1 is mounted in a typical dental lighting standard or fixture 11 having a moveable arm 12 and handle 13 for adjusting the position of the reflector in space. A shield 14 houses a lighting element, not shown in FIG. 1 but illustrated elsewhere, which lighting element produces illumination which is reflected by the dental reflector 10 into a pattern 32 shown schematically as dotted lines 15, 16, 17, and 18. It should be understood that the pattern 32 outlined in FIG. 1 is schematic and that the actual pattern will vary somewhat but will be generally confined to an oblong pattern of certain limited and predictable dimensions.

Figure 8:
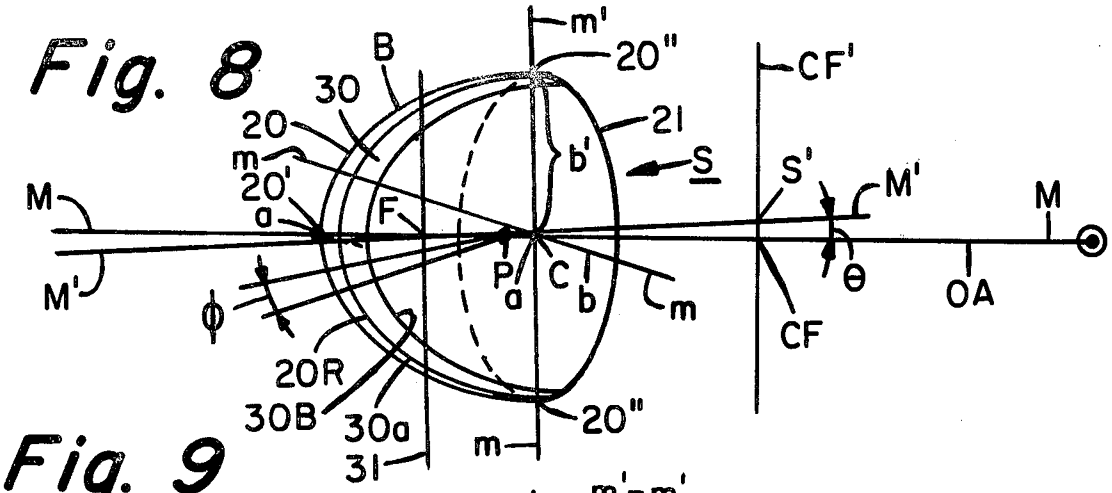
FIG. 8 is a schematic representation illustrating the manner in which the base elipsoidal surface is sectioned and rotated.

The compound elipsoidal reflector 10 is in the form of segmented portions of at least one base elipsoid derived from an elipse of revolution. An elipse of revolution is conveniently illustrated in FIG. 8. An eliptical curve 20 with end points 20′-20″, having a focus at F, and a major axis of length $2a$ along line M—M, is rotated 360° (180° if the limits 20″-20″ are used) to form a base surface S. In FIG. 8 the major axis M—M, passes through the principal focus F and conjugate focus CF, while a minor axis of length $2b$ m—m, lying in a horizontal plane perpendicular to M—M, passes through the center of the elipse at C. Line m′—m′ of length $2b'$, perpendicular to lines m—m and M—M, passes through C and lies in a vertical plane. It should be understood that base surface S is a portion of an entire elipsoid, only part of which is shown herein.

The base surface S contemplated in the present invention is a regular surface, i.e., it is symmetrical about point C in the direction of rotation of the elipse of revolution 20. In other words the path of points 20″ form a circle 21 of radius b′ when rotated. Any plane intersecting the base surface S, which plane is parallel to the minor axis m—m and perpendicular to the major axis M—M (i.e. lying in plane m—m, m′—m′), will form a series of concentric circles when viewed in the direction of the major axis M—M. In a regular elipsoid minor axis m—m may be in any orientation in the plane of circle 21 since $b=b'$.

The reflector 10 and all base surfaces and curves referred to below will have a principal focus, hereinafter referred to as F and a conjugate focus, hereinafter referred to as CF, as well as a skew conjugate focus CF′ which results from rotation of the base elipsoid through a selected angle $\theta$, (M—F—M′) which rotation is illustrated in various forms in FIGS. 8-15.

Figure 2:
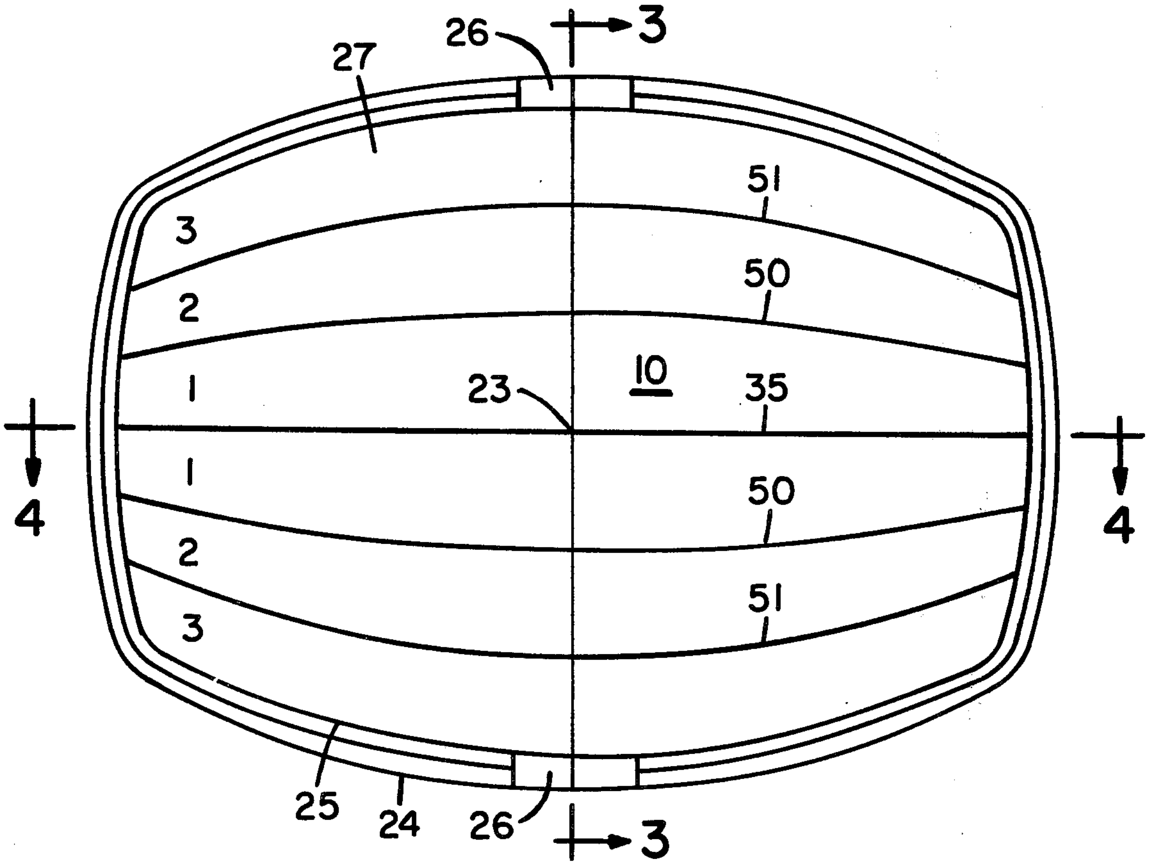
FIG. 2 is a frontal view of an embodiment of the reflector of the present invention.

In FIG. 2 a frontal view of the reflector 10 of the present invention is shown. In a preferred embodiment the reflector 10 is divided into sections 1-3 to one side of line 4—4 and sections 1-3 to the other side of line 4—4. The sections 1-3 to either side of line 4—4 have the same reference numerals because in the preferred embodiment the sections 1-3 are substantially the mirror image of the other similarly numbered sections, so as to provide a symmetrical reflective pattern relative to line 4—4, passing through line 3—3, at the central portion 23 of the reflector 10. The surfaces 1-3 will hereinafter be referred to as surfaces or sections 1-3 unless reference to a specific one is required. The sections 1-3 are derived from at least one base elipsoidal surface S illustrated in FIG. 8, being selected sectors taken from the surface of the base elipsoid S in accordance with the principles of the present invention.

The reflector 10 in FIG. 2 has a main reflector surface 27, an outer edge 24 and inner edge 25 forming a finished portion or frame of the outer section of the reflector 10. In addition, integral bosses are formed at 26 which are adapted to engage with suitable clamps or receivers (not shown) in the lighting fixture 11, illustrated schematically in FIG. 1.

Figure 3:
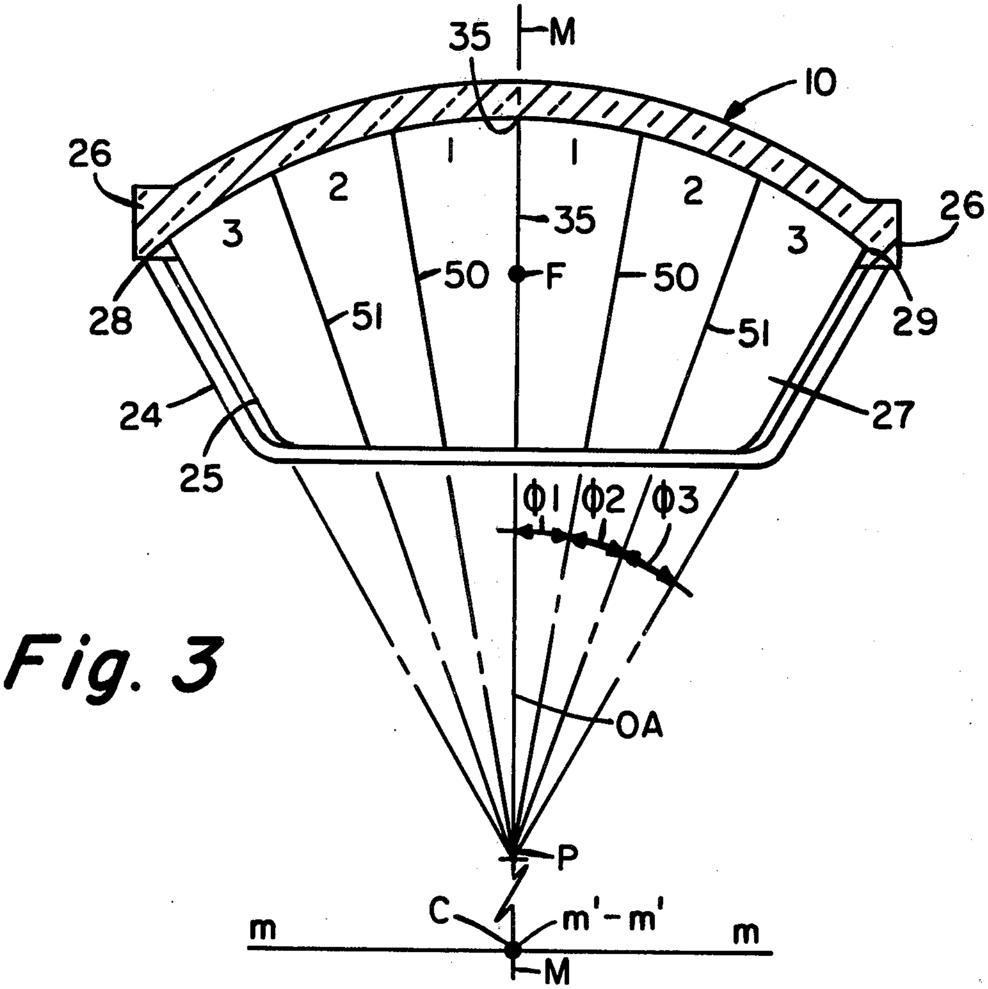
FIG. 3 is a sectional view taken along line 3—3 of FIG. 2.

FIG. 3 shows the lighting reflector 10 of the present invention sectioned along line 3—3 of FIG. 2. In this view the line M—M corresponds to the major axis of the unrotated base elipse B shown in FIG. 9; line m—m, the minor axis; and point P, a convenient place to establish an angular measurement. The line M—M may be referred to as the optical axis OA of the system.

FIG. 3 illustrates the separation of sections 1-3. Each section 1-3 is of a selected arc length as measured by respective angles $\phi 1$-$\phi 3$. In one embodiment each angle $\phi 1$-$\phi 3$ is the same for each section 1-3. It should be understood that $\phi 1$-$\phi 3$ could be different for each section 1-3 as discussed below.

Figure 4:
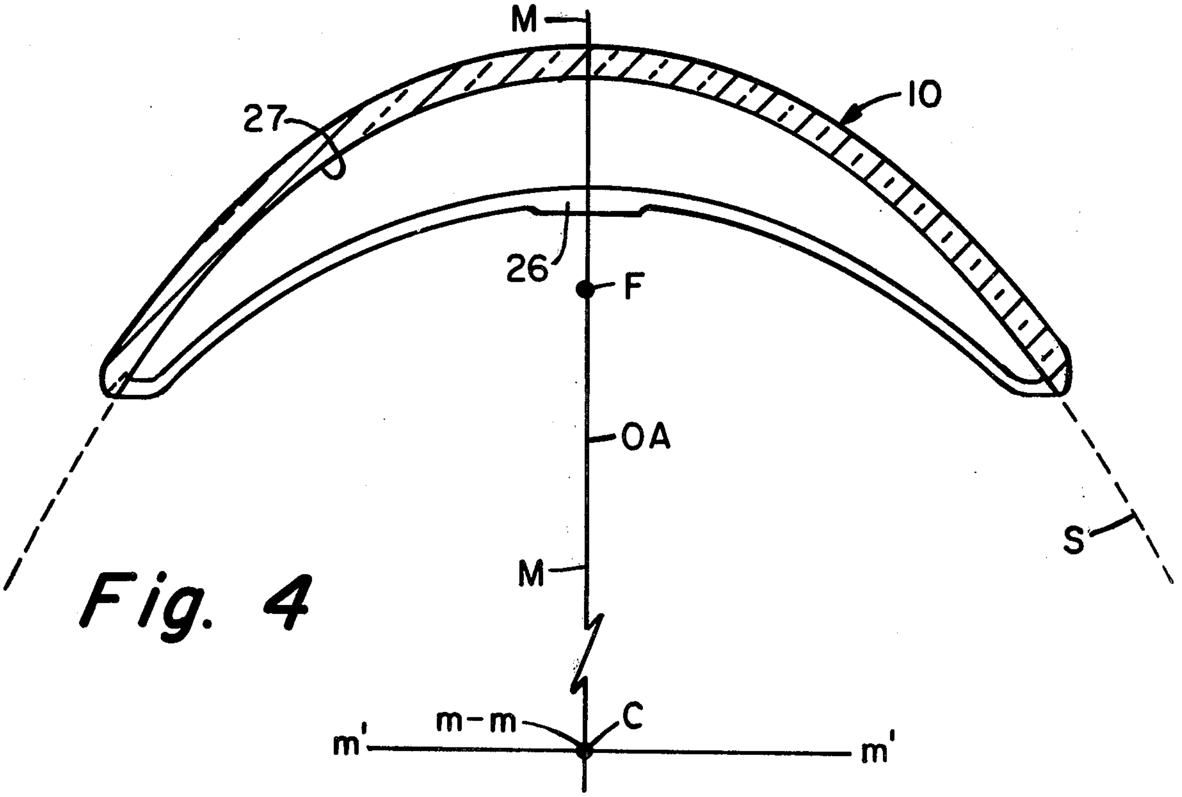
FIG. 4 is a sectional view taken along line 4—4 of FIG. 2.

FIG. 4 shows a view of FIG. 2 along line 4—4. The shape of base elipsoid surface S as rotated into a plane defined by lines M—M, m′—m′ is illustrated. The curve of surface S in the plane is superimposed in dotted lines to illustrate the shape of the reflector 10, in cross section, in relation to the base surface.

The surface 27 of the reflector 10 illustrated in FIGS. 1 through 4 is in the form of a compound elipsoid. In the present invention the term means that the reflector is formed from portions of at least one base elipsoidal surface S which portions are aligned adjacent one another to form a surface which has regions or sections. Each section or region 1-3 is a selected section of the base elipsoid S which is illustrated in FIG. 8. For example, section 30 is a sector of the base surface S which may be formed by two planes intersecting the surface S at angle $\phi$ measured from point P on optical axis M—M. The planes cross surface S along curves **30*a* and 30*b* and the surface 30 is rotated about an axis 31 which axis is perpendicular to a plane including major axis M—M and minor axis m—m and passes through focus F. The angle of rotation about axis 31 is shown in FIG. 8 as reference angle $\theta$. Additional sections of the base elipsoid S may be formed in a similar manner with other planes intersecting the surface S forming the respective sections 1-3. The sections are thereafter aligned adjacent one another, with reference to primary focus F, to form the reflector surface 27** with a conjugate at S′.

Figure 9:
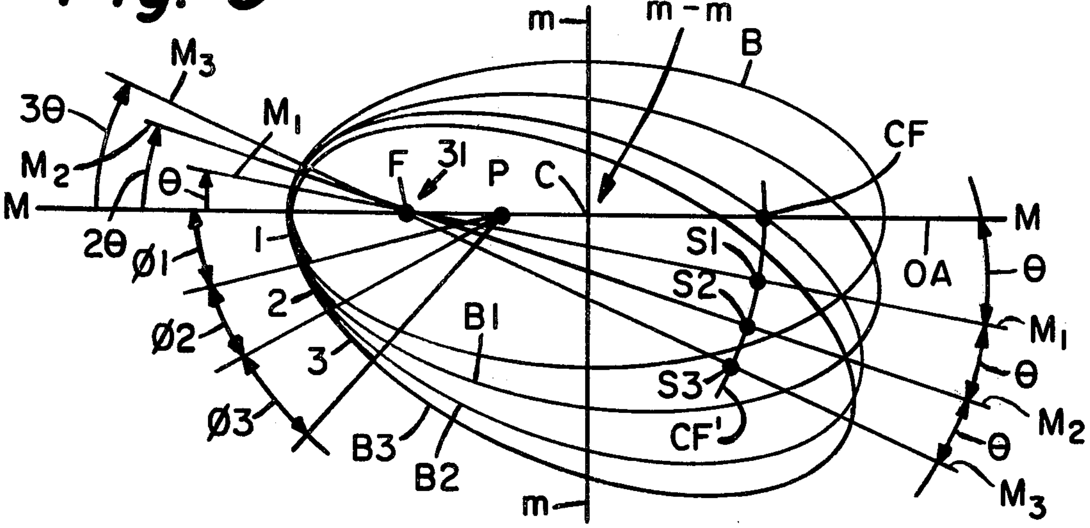
FIG. 9 is a representation in a plane view showing the graphic solution to the derived surface of the present invention.
Figure 10:
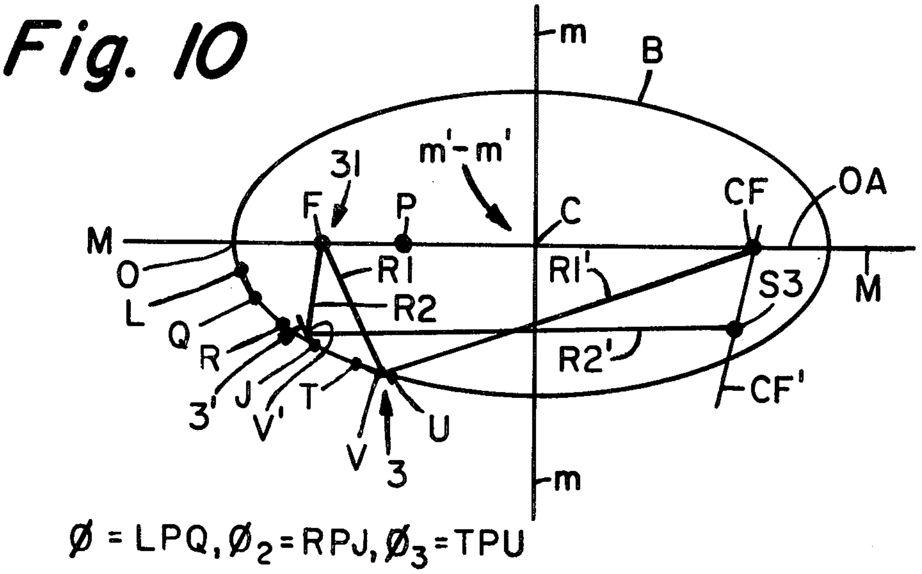
FIG. 10 is another graphic solution for deriving the reflector surface of the present invention.
Figure 11:
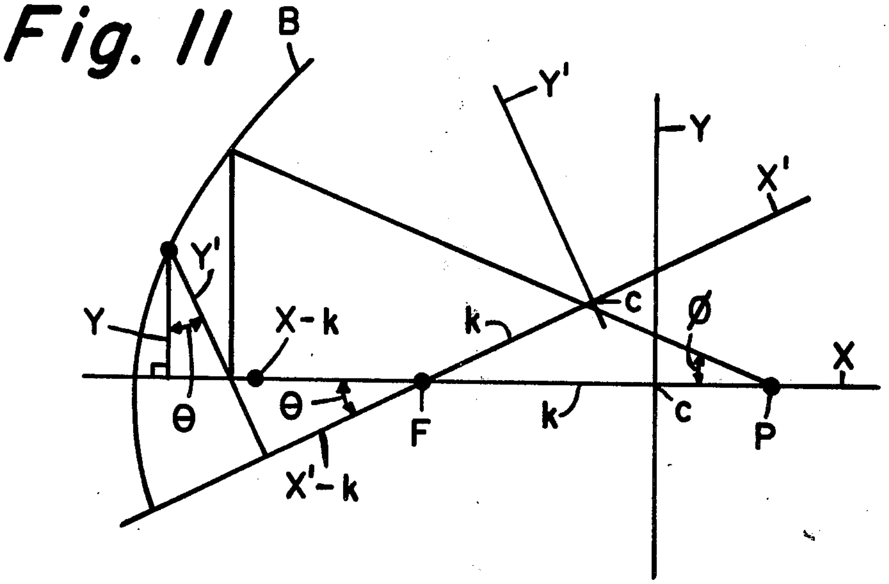
FIG. 11 is an illustration of two coordinate axis systems, one rotated $\theta°$ relative one to the other about a point F.

FIGS. 9, and 10 illustrate graphic solutions used to derive the surfaces of reflector 10 of the present invention. In FIG. 9 a base elipse B is shown aligned with the major and minor axes M—M and m—m respectively, with a center at C, the primary focus at F, and conjugate CF. The base elipse B is rotated through angle $(n)\theta$, where $n=1,2,3 \ldots$, about point F, so that the conjugate focus CF traces a path along the curve CF-CF′. In a preferred embodiment (n) is an integer, however (n) need not be so defined for every application of the present invention. A point along the said curve CF-CF′ becomes a skew conjugate focus S1, S2, S3 for a respective corresponding angle of rotation $(n)\theta$, $(n=1,2,3)$, of the base elipse B, to positions of rotated elipses B1, B2, B3 in the plane shown. It is important that the sections 1-3 have the same primary focus F so that the light source may be placed at the convenient location in the lighting fixture. This may vary however as will be discussed below.

In the graphic solution illustrated in FIG. 9 there is shown an axis of rotation 31, perpendicular to the plane of the page, positioned at the primary focus F of the base elipse B. Thereafter the base elipse is rotated through the angle $\theta$, (M—F—M1), about axis 31 at point F. The rotation of base elipse B moves the conjugate focus CF to skew point S1 along the curve CF-CF′, which corresponds to rotated base elipse B1.

To establish skew points S2 and S3 the base elipse B is rotated to positions B2 and B3 to establish respective anbles $2\theta$, (M—F—M2) and $3\theta$, (M—F—M3). Selected progressive sections 1-2 and 3 are chosen from the rotated base elipse B at positions corresponding to the location of elipses B1, B2 and B3. Elipse B3 provides section 3 for the angle $\phi 3$ measured from point P and displaced $3\theta$ from line M—M. Section 3 has its skew conjugate focus CF′ at point S3. Sections 1 and 2 are similarly defined from respective elipses B1 and B2.

A second graphic solution is illustrated in FIG. 10, wherein sections of the base elipse B are fragmented from a measuring point P at various angles $\phi 1$-$\phi 3$ defined in the legend adjacent the drawing. Sections 1-3 in FIG. 10 are rotated clockwise into the major axis M—M about line 31 passing through the primary focus F. The theory of the graphic solution of FIG. 10 is the same as for FIG. 9. The execution being different for illustrative purposes only.

The method of the solution is, to select a segment of an elipsoid, and rotate same about one focus until the desired position of the conjugate focus is reached. E.g. section 3 in FIG. 10 is an arc segment of $\phi 3$ degrees of the angle T—P—U of elipse B. The position of point T lies on the base elipse curve B a distance defined by $3\theta+\phi 1+\phi 2$ whereas point U is located at $3\theta+\phi 1+\phi 2+\phi 3$. If the section 3 is rotated clockwise about F by $3\theta$ to position 3′, the conjugate focus for section 3′ will occur at S3, as illustrated by the shift of ray R1—R1′ (F—V—CF) to R2—R2′ (F—V′—S3), the angle between R1 and R2 for corresponding respective points of intersection V—V′ with the curves 3, 3′ being $3\theta$.

A mathematical formulation may be derived to provide the basis for reproduction of the desired surface utilizing the parameters for the base elipsoidal surface and transforming the co-ordinates. Such a transformation might include the linear transformation of the center point of the elipsoid to one focus thereof and the rotation of the elipse about that point described in terms of trigonometric functions. Once the mathematical transformation is known, an expression for segments of the base surface may be derived and any point thereon may be found by calculation. It should be understood that the above graphic solutions are described for one base elipse B. The mathematical solution described below will illustrate many possible variations.

In accordance with principles of analytic geometry the relationship of points in one coordinate axis system may be described in terms of another system. For example in FIG. 11, let B be the base elipse; x, y are axes lying along respective the major and minor axes of the reflector; x′, y′ are axes lying at an angle $\theta$ relative to x, y; the angle $\theta$ is measured at a point F, a distance k from the origin C measured along x.

x, y may be expressed in terms of x′, y′ as follows:

$x=(x'-k)\cos\theta+y'\sin\theta+k$ $y=y'\cos\theta-(x'-k)\sin\theta$ x′,y′ in terms of x and y:

$x'=(x-k)\cos\theta-y\sin\theta+k$ $y'=(x-k)\sin\theta+y\cos\theta$

From the above expressions any point on the curve B may be expressed in terms of either x,y or x′,y′.

The general expression for an elipsoid is $$x^2/a^2+y^2/b^2+z^2/c^2=1$$

where a is one half the major axis along x, b is one half the minor axis along y and c is one half the minor axis along z. For the base surface in question, b and c are equal. Further if the analysis is made in the x,y plane, z=0, and the above expression reduces to the equation for an elipse, namely:

$$x^2/a^2+y^2/b^2=1$$

This relation is used to solve for various values of a and b, as the surface is analyzed.

In a first embodiment discussed with respect to FIGS. 9-10 it was assumed that the focus F was the point of rotation for the base surface. In practice however the reflector 10 does not have one focus F, but has a plurality of shifted focii in the vicinity of the focus F of base surface B. The reason for the shift is that in order to obtain a smooth contour for the surface 27 of reflector 10, the sections 1-3 were aligned so that the surface 27 appears continuous.

Figure 12:
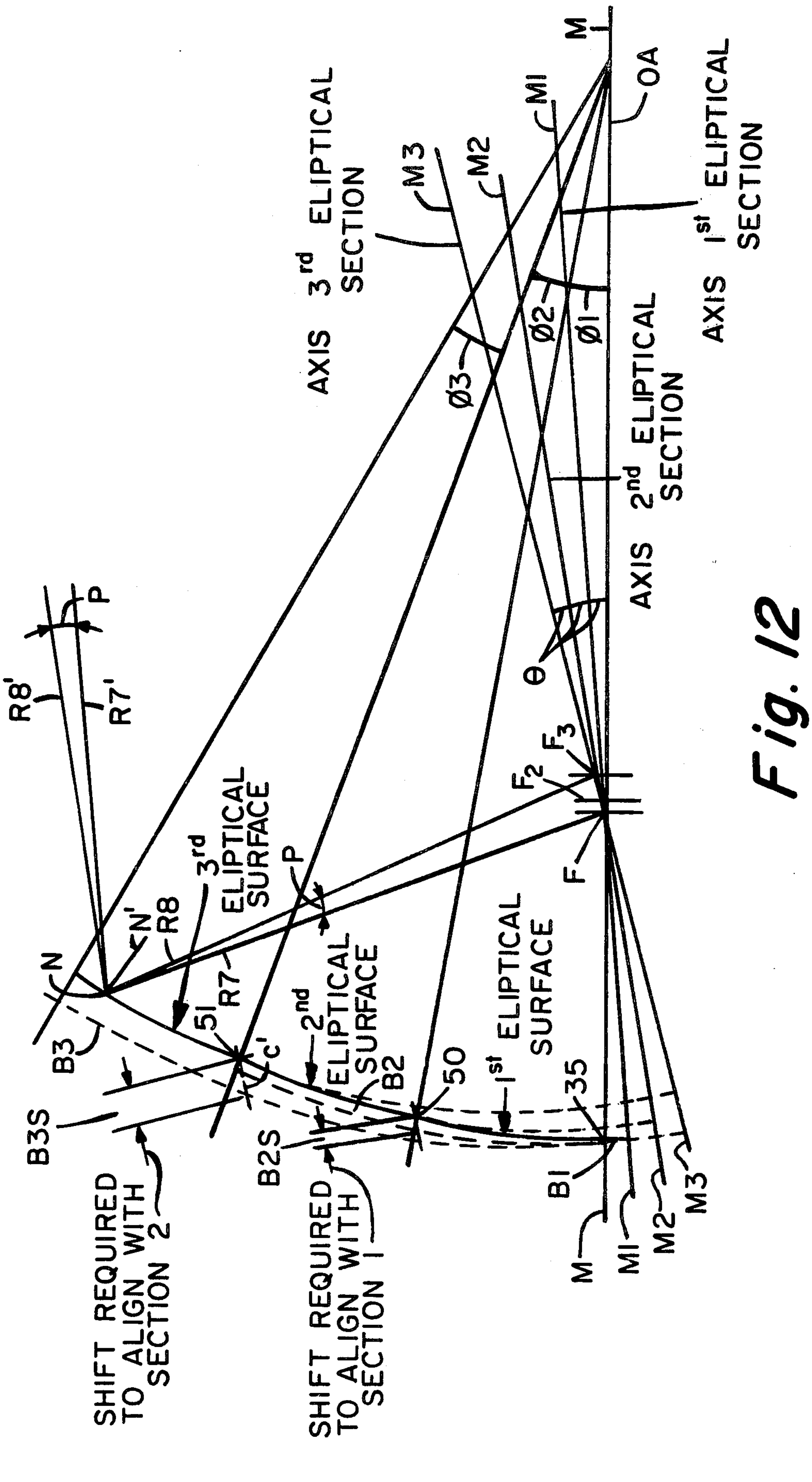
FIG. 12 is an illustration of the construction of various base elipse curves and their relation to a focal shift.

FIG. 12 illustrates the concept. It can be clearly seen that first section 1 of reflector 10 is a section of base surface B and labeled B1 for clarity. That is, B1 is surface B rotated $\theta°$ about point F. Section 2 is a portion of base surface B rotated $2\theta°$ and referenced at B2, and similarly section 3 is a portion of base surface B rotated $3\theta$. Note however that the true position for section 1-3 may not be coincidental with respective base surfaces B1-B3. In FIG. 12 for example section 2 is shifted from surface B2 to the right by B2S as shown. This allows the surface 27 to be relatively smooth at point 50. Likewise section 3 lies no longer in surface B3 but is shifted to the right by B3S so that surface 27 is smooth at 51. Points 50 and 51 are transition points from sections 1 to 2 and 2 to 3 respectively.

Note that in the vicinity of the focus F other focal points are referred by F2 and F3. The shift in respective focii from F for section 1 to F2 for section 2 and F3 for section 3 is caused by the shift of each of the respective sections noted above.

Figure 13:
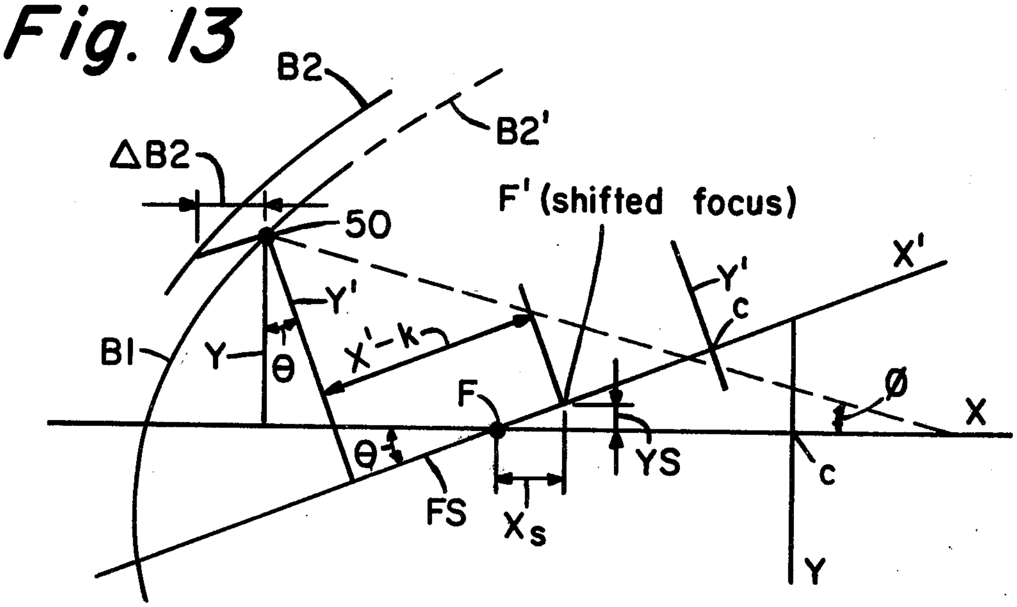
FIG. 13 is an illustration of the focal shift in relation to a pair of coordinate axis systems rotated by $\theta°$ relative to the other at a point F.

The shift in focus from F to F′ may be expressed by the following expression from FIG. 13.

$x\text{ shift}=x_s=(x'-k)-F_s$ $y\text{ shift}=y_s=(x-k-F_s)\sin\theta,$ where:

$$F_s=y'+(y')^2-4\tan\theta(xy-y\tan\theta)$$

The The calculation for the focus shift may be carried out to determine if the shift is too great for the accuracy desired. For example, in FIG. 12 the effect of a focal shift is illustrated. A ray R7 illuminating from Focus F is reflected at point N in section 3, as R7′. A ray R8 emanating from shifted focus F3 is reflected at N in section 3 as R8′. Note the shift of the ray R8′ by angle p. As the distance from the surface 3 increases p becomes more divergent. For small shift in focus p may be negligible. On the other hand if the focal shift has adverse affect on the quality of the resultant illumination at the conjugate along CF-CF′ then a correction may be made as discussed below.

Figure 14:
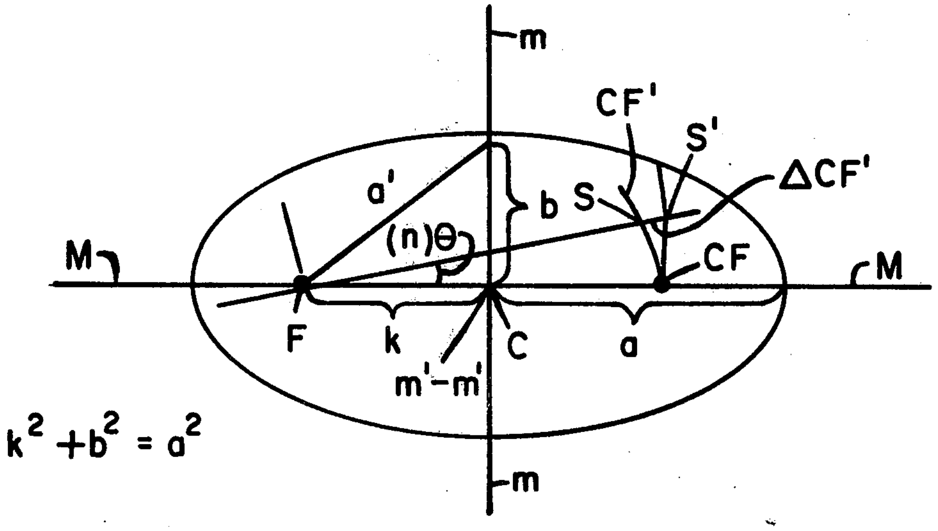
FIG. 14 is an illustration of some basic parameters of an elipse in graphic form.

From FIG. 14 the fundamental relations of an elipse may be evaluated. The value a, (½ major axis M—M) and b, (½ minor axis m—m) are given, the distance $2k$ from the focus F of elipse B to the conjugate focus CF is given, and the hypotenuse (a′), of right triangle k,b,a′, equals a.

From FIG. 13, in order to keep focus F fixed for each corresponding section 1-3 of the surface 27, each base surface B1-B3 must be recalculated.

Beginning with the initial base surface B as a given, (see FIG. 12), let B=B1. Then at a point on curve B1, i.e. 50, the limit of the section 1 is reached (e.g. at angle $\phi 1$). At this point 50 a transition occurs. In order to provide smooth transition from section 1 to section 2, either base surface B2 must be shifted by B2S with a consequential shift in focus to F2, or a new base surface B2′ may be calculated. From FIG. 14 point S′ lies along curve CF–CF′, the point S′ is the ideal position for a conjugate of F, and the distance from F to S′ equals $$S'-F=2k/\cos(n)\theta$$

where $n=1,2,3\ldots$ and $$k^2+b^2=a'^2=a^2$$

for a given (k), a and b may be calculated.

Knowing a, b and k and the position of focus F, an expression for an elipse having those constraints may be calculated.

The coordinates of the elipse so calculated, having a point in common with 50, in FIG. 12, may be transformed to x′,y′ expressions in order to define the curve B2′, as rotated through an angle of $(n)\theta$ wherein $n=2$ for the section 2. Likewise section 3 may be described with the knowledge of the position of point 51, (see FIG. 12) and the parameters given above. It should be noted that points along boundaries 50 and 51 between respective sections 1–2 and 2–3 as well as point 35 for sections 1—1 (see FIGS. 2, 3, 5, 6, and 12) are mathematically equivalent. That is all points share mathematical characteristics which are common to the respective sections along the particular boundary if the aforementioned correction is made.

Figure 15:
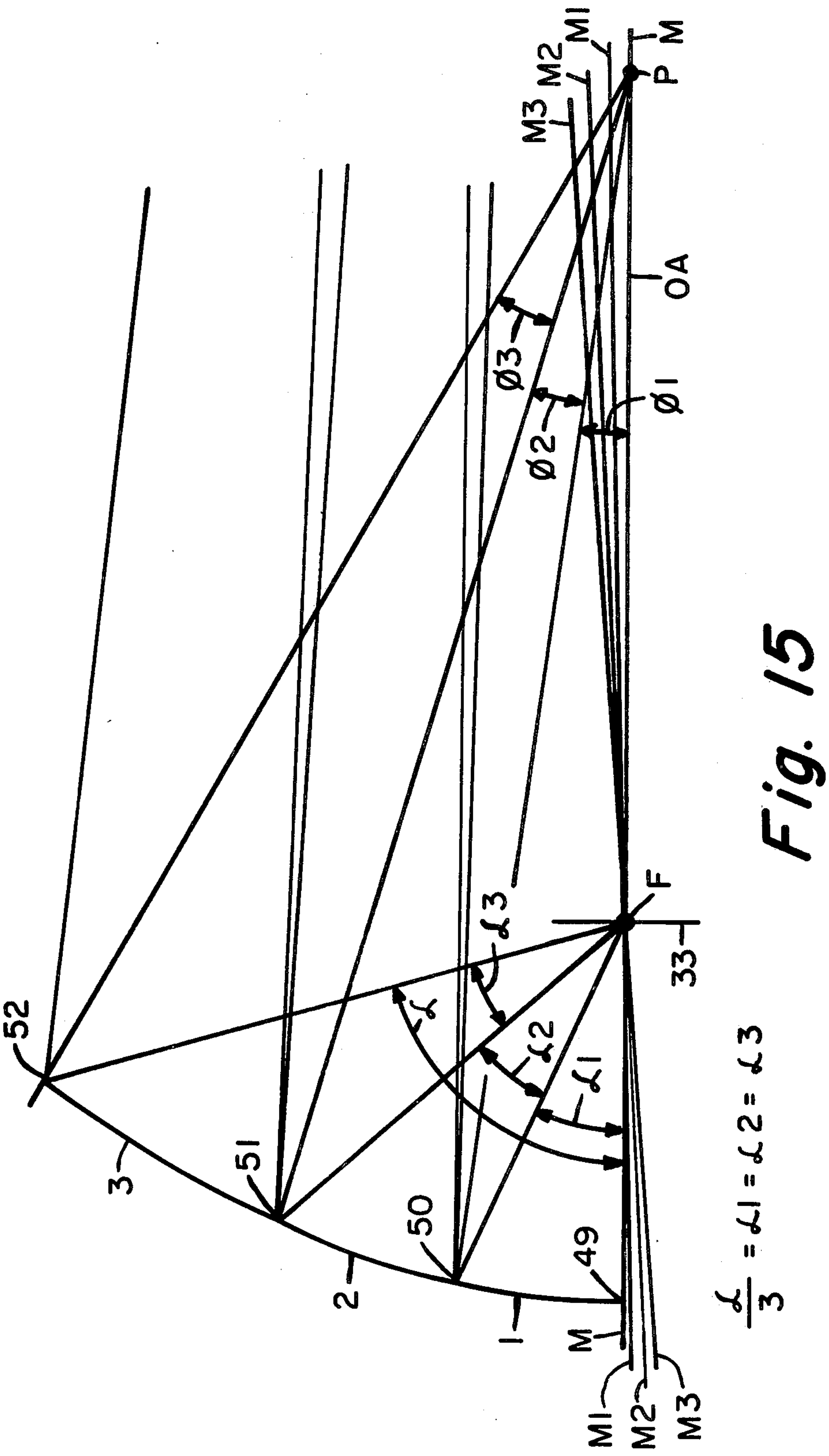
FIG. 15 is an illustration of a modification of the surface of the reflector by variation of the projection of sections of said surface relative to the light source.

In FIG. 15 there is illustrated a variation of the present invention wherein each angle $\phi 1$–$\phi 3$ determining the arcuate length of sections 1–3 may be modified. In certain applications $\phi 1=\phi 2=\phi 3$, however, if more uniform illumination is required $\phi 1$–$\phi 3$ are varied to achieve the desired result. To accomplish this, the arc lengths of sections 1–3 should be increased as the distance from the major axis M—M increases. Note that the projection of arc length 49–50 of section 1 relative to focus F would be different from the respective projections of arc lengths 50–51 and 51–52 of sections 2 and 3, if $\phi 1$–$\phi 3$ are the same for each respective section. The projection of each section may be equalized so that the light source 33 sees the same field for each section 1–3 relative to focus F. This may be accomplished by establishing the entire arc length of the reflector 10 between points 49 and 52 relative to focus F by angle $\alpha/(m)$ where $(m)=1,2,3\ldots$ Thereafter angle $\alpha$ may be divided by the number of sections m ($m=3$) yielding angles $\alpha/3$ for $\alpha 1$–$\alpha 3$ as illustrated. The angles $\phi 1$–$\phi 3$ described previously have been measured from a point P which is chosen for convenience of calculation to lie on the optical axis M—M such that the total angle for one side of the reflector is 30° (i.e. angle 49—P—52 $30°=\phi 1+\phi 2+\phi 3$). The variation of $\phi 1\phi$-3 illustrates a refinement of the surface construction of the reflector 10, which may be utilized when variation in the intensity of the illumination zone is to be further controlled.

From the foregoing it is clear that many variations of the surface 27 of reflector 10 can be accomplished by manipulation of the parameters of the base surface. Further it should be understood that any or all of the parameters may be varied for each section including the exponents of x,y and z for the fundamental relation of the elipsoid.

Figure 5:
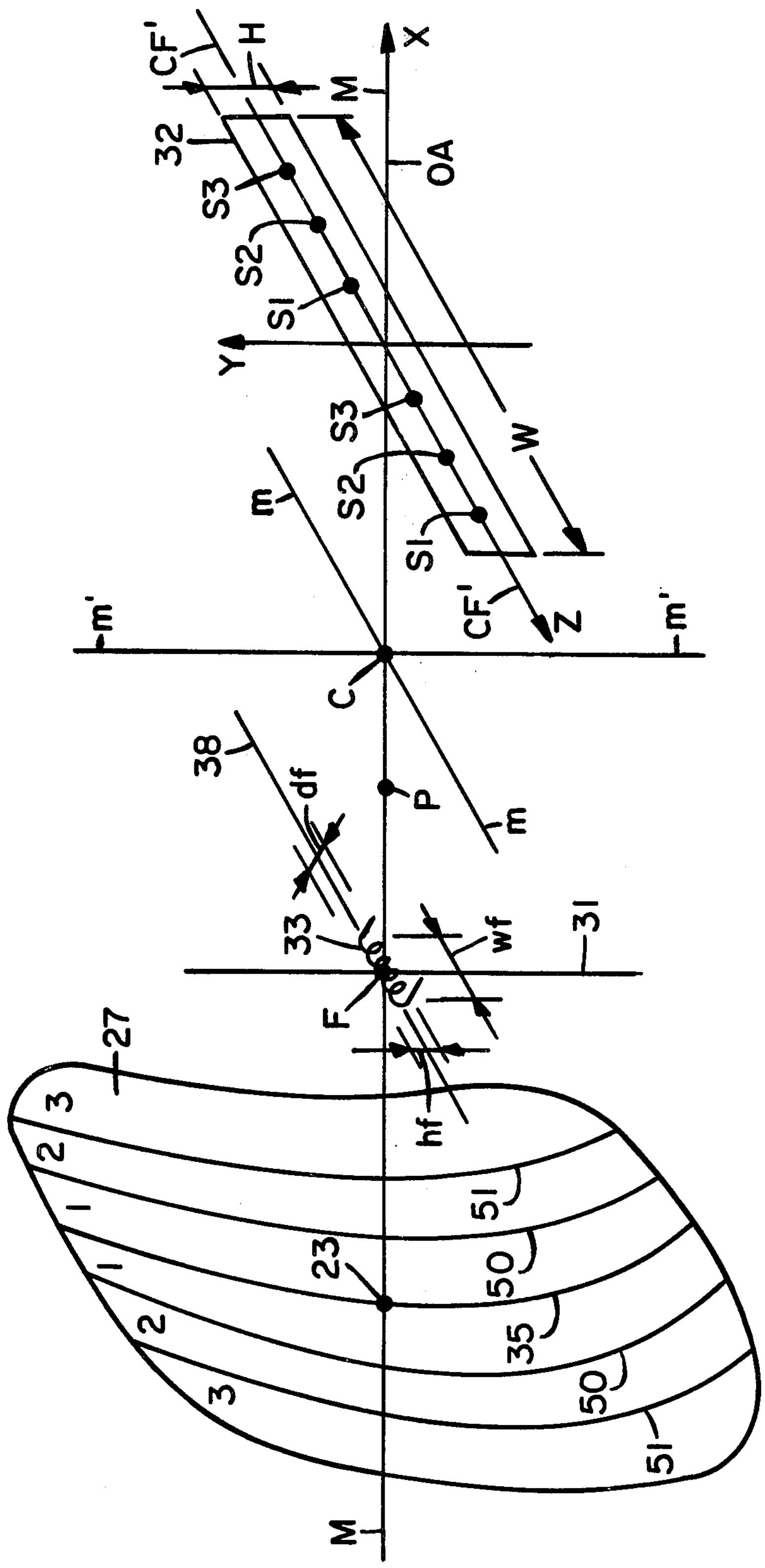
FIG. 5 is a schematic representation showing the alignment and geometry of the reflector of the present invention with respect to the required light beam pattern.

In FIG. 5 a schematic drawing illustrates the configuration of the illumination zone 32 (outlined as 15–18 in FIG. 1) which is produced by the application of the principles set forth herein. Assume for convenience an orthogonal x,y-z coordinate system as illustrated. Zone 32 is elongated along the z axis and is somewhat narrower in the y direction. The zone 32 in reality is somewhat curved as illustrated in FIGS. 9 and 14 (see line CF–CF′), however, for purposes of the application as a dental reflector, the zone of illumination 32 may be shown as lying in a plane (y-z plane). The curvature of CF–CF′ is not necessarily critical but may be calculated and corrected if desired. Assume however, that respective conjugate focii S1–S3 for sections 1–3 lie, within required accuracy, along CF–CF′ in the vicinity of the zone 32. The zone 32 is aligned with, and substantially parallel to, a longitudinal axis 38 of the light source or filament 33.

The spread of the beam pattern is caused by the displacement of the conjugate focii CF′ in the z direction by the rotation of the sections 1–3 through angle $(n)\theta$ when $(n)=1,2,3$ for respective 1–3. The physical size of the filament 33, in x,y and z directions also causes spread of the beam, but not so pronounced as by the modification of the base surface S. The width W of the illumination zone 32 along the z axis, is partly a function of the width wf of the filament 33 but primarily caused by the rotation of the elipsoid sections and controlled skew of the conjugate focus. The height H of the zone 32 in the y direction is primarily a function of the height hf of the filament 33 in the Y direction.

The shape of the zone 32 is convenient for dental work in that it covers the mouth area of the patient when aligned properly and avoids shining light into the patient's eyes, thereby assisting the dentist to perform the surgical procedure and providing as much comfort as possible to the patient under the circumstances. Variation of the intensity of light in the x direction will be discussed further below.

Figure 6:
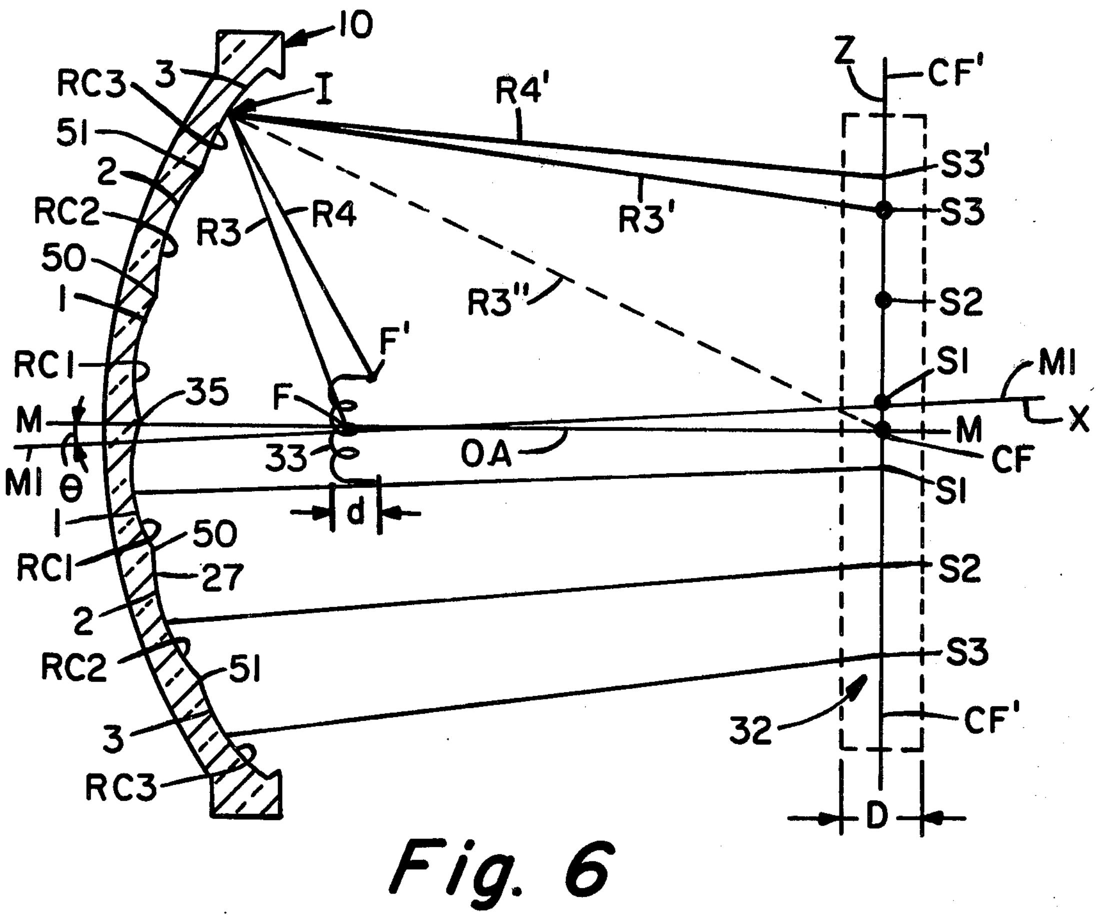
FIG. 6 is a schematic representation which exaggerates the contour of a portion of the reflector surface lying in a plane including the lines 3—3 and 4—4, which exaggeration is for illustrative purposes.

FIG. 6 illustrates in a somewhat exaggerated form the shape of the surface 27 of reflector 10, and rotation of the conjugate focus to various points in the zone 32 along CF–CF′. The depth D of the zone 32 in the M—M direction (x direction of FIG. 5) is governed by the depth df of the filament 33 in the M—M direction. Further if the correction discussed above relative to the shift of the focus is neither calculated nor corrected (see FIG. 12), there is experienced a variation of the intensity of illumination in the x direction when the reflector sections are aligned to provide a reasonably smooth surface 27.

Each section 1–3 has a corresponding curvature RC1–RC3 illustrated in FIG. 6, and each is exaggerated for purposes of illustration. RC1–RC3 represent a curvature for each respective eliptical section 1–3 in the horizontal plane (x-z plane of FIG. 5), as derived from the graphical solutions illustrated in FIGS. 8 through 10 or as calculated by the transformations discussed above. The curvature RC1–RC3 for each section 1–3 are exaggerated in order to illustrate the topical surface of the reflector 10. Since the sections 1–3 are elipsoidal sections the curvature RC of each respective section 1–3 varies but predictable for any projected section taken.

Each surface 1–3 has a primary focus in the vicinity of F since the base elipse B is rotated about the point F. Their respective conjugate focii CF lie along CF–CF′ as determined by $(n)\theta$. Section 1 of the reflector 10 (above line M—M) is rotated counterclockwise to position M1—M1 to move the conjugate focus from CF to S1. Likewise respective sections 2 and 3 above line M—M are similarly rotated counterclockwise through (n)$\theta$°. Section 1-3 below line M—M are rotated clockwise (n)$\theta$° to render zone 32 symmetrical about optical axis OA.

To illustrate the effect of the application of the principles of the present invention on light rays, reference to FIG. 6 continues. Any ray R3 leaving a point corresponding to the focus F and impinging on the surface of the reflector 10 at point I will be reflected as ray R3' and follow a path F—I—S3. Whereas the same ray R3 would reflect as R3'' and follow F—I—CF for a normal unrotated elipsoidal surface. If ray R4 leaves an edge of the filament at point F' it will reflect as R4' and follow the path F'—I—S3'. This shift is due in part to the change in the conjugate focus CF to S3 imparted by the rotation of surface 3, and also to the fact that the filament 33 is not a point source. The point S3' is shifted from S3 by a distance proportional to the difference in the positions of F and F'.

Figure 7:
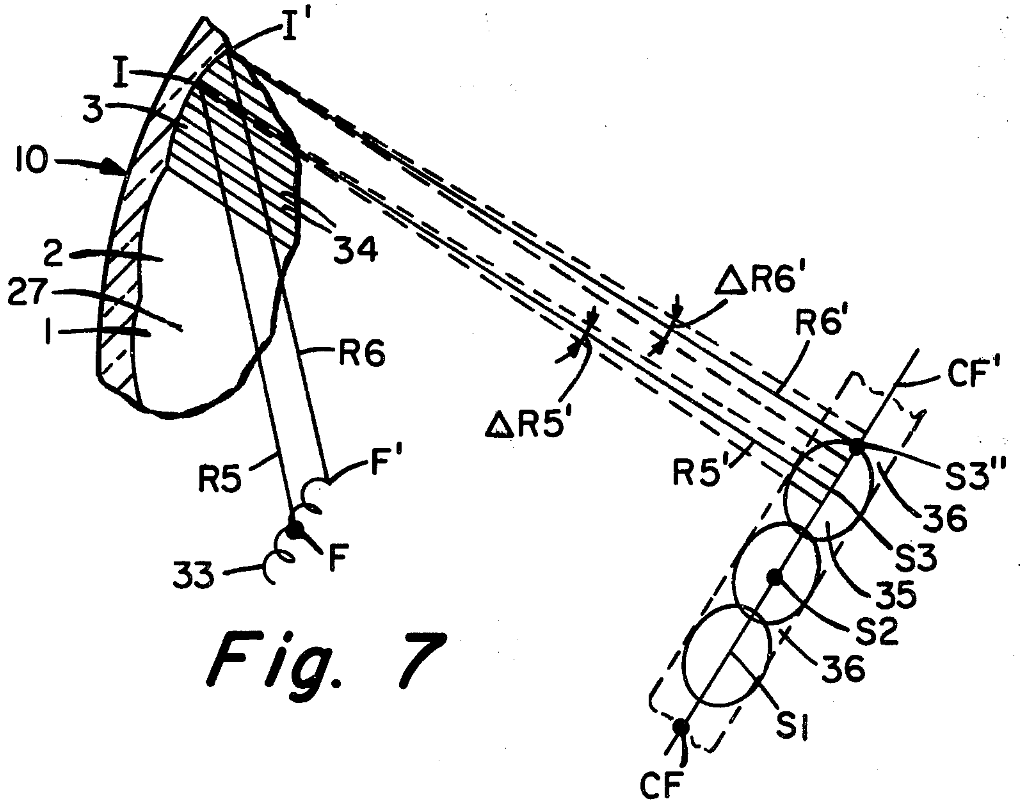
FIG. 7 is a fragmentary view of the compound elipsoidal surface of the present invention, illustrating superimposed diffuser surfaces.

In addition to the spread caused by rotation of section 1-3 and the effects of the light source geometry, another factor is included to enhance the beam spread quality as illustrated in FIG. 7. Ridges 34 are superimposed on the reflector surface 27 so that the rays emanating from the filament 33 will become diffused and thereby softened in the illumination zone 32. The rounded shape of a portion of the beam at 35 illustrates schematically the spreading of the beam as it leaves the surface 27 towards conjugate S3 of section 3. This shape 35 is caused mainly by the variations in the geometry of the filament 33. For example in FIG. 7 R5 leaving filament 33 from F impinges on the surface of the reflector 10 at I, is reflected as ray R5' and follows path F—I—S3. Ray R6 leaves filament 33 at F' and is reflected as ray R6' following path F'—I'—S3''.

Spaces 36 between the patterns 35 are areas which receive lower intensity light due to filament geometry. In order to remedy this, diffuser lines 34 are superimposed onto the reflector surface by appropriate means to create a wash in the area 36 and render the zone 32 more uniform in illumination appearance. The diffuser lines 34 follow generally the same alignment as the planes which were derived to create the section 1-3. The reflected rays R5' and R6' are diffused into respective patterns ΔR5' and ΔR6' as illustrated to create the wash necessary to render the pattern more uniform i.e. to fill the areas 36 with illumination.

In the embodiments discussed herein, the angle (n)$\theta$ corresponding to the rotation of the base ellipse B about F ranges from about 1.5 to about 2.5°. Multiples (1,2,3) of $\theta$ are used to skew the conjugate focii CF of sections 2 and 3 respectively. The arc segment of each section 1-3 is represented by respective angles $\phi$1-$\phi$3. In the preferred embodiment of the present invention $\phi$1 ranges from about 8° to about 10°, $\phi$2 ranges from about 9° to about 10° and $\phi$3 ranges from about 10° to about 13°. Sections 1-3 are aligned adjacent each other so that the total angle of displacement $\phi1+\phi2+\phi3$ from the center of the reflector surface 27 at 35 to either edge of the reflector at points 28 or 29 is about 30°.

The above parameters are for the preferred embodiments discussed above and in no way limit the application of the principles of the present invention to the dimensions.

The surface 27 of the reflector 10 is coated with a selective coating capable of reflecting a substantial portion of the visible radiation produced by the light source and transmitting invisible (infra-red) radiation. The transmission of infra-red is especially helpful to produce cool light and reduce patient discomfort. A substance such as dichroic may be used for the selective coating.

In order to filter ultra-violet radiation the light source 33 may be shielded by a coating deposited on the envelope (not shown). In addition a plastic, ultra-violet absorbing shield (not shown) may be used which, both filters the UV and shields the patient if the light source envelope breaks.

While there has been provided what at present is considered to be the preferred embodiment of the present invention, it will be clear to one skilled in the art that certain changes and modifications may be made therein without departing from the invention, and it is intended by the following claims, to cover all such changes and modifications which fall within the true spirit and scope of the invention.

I claim:

1. Means for reflecting illumination comprising:

a reflector, formed from a plurality of surface segments, each of said surface segments having lateral boundaries for reflecting said illumination into a limited zone of illumination:

each surface segment formed from a portion of at least one elipsoidal base surface forming a compound elipsoidal surface, said base surface having a major axis corresponding to an optical axis for the reflector and a minor axis, said major and minor axes being perpendicular and intersecting at a center point for the base surface, a pair of focci for the base surface lie on said major axis; a first of which being a primary focus, for the reflector, for location of a source of illumination, a second of which being a conjugate focus lying in the vicinity of the illumination zone;

said surface segments being defined as selected portions of said base surface measured from a point on said major axis, said surface segments defined with respect to coordinates corresponding to a displacement of the center point of the base surface to the vicinity of said primary focus and a rotation of said base surface through a selected arc segment about a line substantially perpendicular to a first plane including said major and minor axes, and passing through said first plane in the vicinity of the primary focus, the lateral boundaries of the segments lying in corresponding planes perpendicular to the first plane and converging towards and parallel with the line about which they are rotated.

2. The reflector of claim 1 wherein each of said plurality of surface segments is a defined eliptical surface having a defined curvature relative to said major axis.

3. The reflector of claim 1 wherein each of said plurality of surface segments has a corresponding primary focus and a conjugate focus, each respective primary focus being located in the close vicinity of the primary focus of said reflector corresponding to that of the base surface and each respective conjugate focus being located in the vicinity of said other conjugate focus of the reflector corresponding to that of the base surface, displaced through an arc segment proportional to said arc segment corresponding to the rotation of said base surface.

4. The reflector of claim 3 wherein each of said surface segments are aligned one next to the other such that their respective primary focii are in the vicinity of the primary focus of the reflector at about the location of the source of illumination and their respective conjugate focii are substantially uniformly spread throughout the zone of illumination.

5. The reflector of claim 4 wherein the source of illumination is located along a longitudinal axis, mutually perpendicular with said optical axis and the line about which the base surface is rotated, and the respective conjugate focii of said surface segments lie in the vicinity of a plane parallel to said longitudinal axis of the light source and perpendicular to the optical axis of the reflector.

6. The reflector of claim 5 wherein the spread of said conjugate focii is such as to form an oblong pattern, said pattern aligned with and substantially parallel to said longitudinal axis of the source of illumination.

7. The reflector of claim 1 wherein, diffuser surfaces are superimposed with said compound elipsoidal surface for causing a spread of said reflected illumination throughout the zone of illumination.

8. The reflector of claim 7 wherein said diffuser surfaces are disposed longitudinally and lie in planes substantially parallel with said optical axis said planes being perpendicular to said minor axis.

9. The reflector of claim 3 wherein each of said plurality of surface segments is derived from a corresponding base elipsoidal surface having a corresponding focus which is coincidental with each of the others in accordance with a selected position of each surface segment relative to the others.

10. The reflector of claim 9 wherein each of said sections is aligned, one adjacent the other, such that a boundary between each section exists, which boundary exhibits a characteristic common to the respective surfaces along said boundary.

11. The reflector of claim 10 wherein said characteristic is a substantial mathematical identity of coordinates of a line lying in each adjacent surface along said boundary therebetween.

12. The reflector of claim 3 wherein, each of said surface segments has a respective optical axis, corresponding to the major axis of the base surface as rotated through said selected arc segment, and each respective optical axis is aligned so as to converge as adjacent lines toward the zone of illumination.

13. The reflector of claim 3 wherein surface segments are disposed in complimentary pairs symmetrically about the major axis, and each complimentary surface segment being selected from the same complimentary portion of the base elipsoidal surface and having the same curvature as its compliment in projection so as to produce a symmetrical oblong pattern of reflected illumination.

14. The reflector of claim 13 wherein the optical axis of each of said complimentary pairs of surface segments corresponds to a rotation of the base surface through progressively larger angles from about 1.5° to about 7.5° as measured from the primary focus of said base surface.

15. The reflector of claim 14 wherein said selected arc segment of rotation is symmetrical about a plane including the optical and minor axes.

16. The reflector of claim 13 wherein the selected portions of the base surface correspond to surface segments of about 8° to about 13° measured from said point on the major axis.

17. An optical system adapted to be mounted in a lighting fixture for providing illumination of a limited zone extending from a relatively limited angle about one plane and a relatively larger angle about a second plane said first and second planes intersecting and being substantially perpendicular one to the other, said optical system comprising:

a lamp filament being operable to produce light rays, mounted in said lighting fixture, having a longitudinal axis both lying in said first plane and perpendicular to said second plane said lamp filament having at least one axis being substantially parallel to said zone of illumination, a reflector having an optical axis lying along a line formed by the intersection of said first and second planes, said reflector being mounted in said lighting fixture adjacent said lamp filament, said reflector having a focal zone in the vicinity of said lamp filament such that the lamp filament and focal zone of the reflector substantially coincide in the vicinity of said optical axis, said reflector being adapted to intercept a portion of the light rays produced by said lamp filament and reflect said light rays into said limited zone, said reflector having a shape corresponding to portions of a compound elipsoidal surface, being described as a plurality of adjacent selected surface segments of at least one elipsoid formed by revolution of an elipse about its axis, each segment having a defined curvature, and each being aligned one adjacent the other so as to reflect light rays impinging thereon respectively toward said limited zone in a converging direction as adjacent beams of reflected light, each of said surface segments of the elipsoid being rotated about a line orthogonal with the optical axis of the reflector and the longitudinal axis of the lamp filament in the vicinity of the focal zone, and having laterial boundaries lying in planes converging along a line which is parallel with the line about which the segments are rotated.

18. The optical system of claim 17 wherein said optical axis intersects the longitudinal axis of the lamp filament in the vicinity of the focal zone and the surface segments each have a corresponding primary and secondary focus, each primary focus lying in the vicinity of the aforementioned focal zone, and each secondary focus lying in the vicinity of the illumination zone.

19. The optical system of claim 18 wherein each of said surface segments are formed in complimentary pairs, one of each pair arranged on opposite sides of the optical axis and extending away therefrom, corresponding to its compliment, and each surface segment, on each side of said optical axis, being juxtaposed to a next one of a complimentary pair, having its compliment in sequence on the other side of said optical axis.

20. The optical system of claim 18 wherein each surface segment of the reflector has its own corresponding optical axis and the corresponding primary and secondary focii lie along said corresponding optical axis for each surface segment, each of said surface segments are aligned such that, their corresponding optical axis cross the zone of illumination at different selected points therein.

21. The optical system of claim 20 wherein said alignment of the corresponding optical axes of the surface segments is in the form of adjacent converging lines, so as to cross the zone of illumination, along a path in substantially parallel alignment with the aforementioned axis of the lamp filament.

22. The optical system of claim 20 wherein the lighting fixture is dental equipment and the illumination zone is illuminated so as to correspond to a patient's mouth area, with insignificant illumination in adjacent areas.

23. In a lighting device for illuminating a selected location, means for reflecting illumination comprising:

a light reflector having an axis lying along a line formed by the intersection of perpendicular first and second planes, said reflector having conjugate focal zones spaced away therefrom along said axis, said reflector being adapted to intercept illumination emanating from a one conjugate focal zone closer to the reflector to reflect said illumination into the other conjugate focal zone, said reflector having a shape corresponding to portions of a compound elipsoidal surface, being described as a plurality of adjacent selected surface segments of at least one elipsoidal base surface formed by revolution of an elipse about an axis corresponding to that formed by the intersection of the first and second planes, said surface segments being portions of the base surface selected from the vicinity of the closer focal zone along the axis and having lateral boundaries lying in planes intersecting along a line passing perpendicularly through the axis and parallel with said second plane, each segment having a defined curvature, and each being aligned one adjacent the other so as to reflect light rays impinging thereon respectively towards the other conjugate focal zone in a converging direction as adjacent beams of reflected illumination.

24. A light reflector comprising:

a reflector surface, formed from a plurality of surface segments adapted to intercept light emanating from a source of illumination into a limited zone spaced around a lateral line;

each surface segment formed from a portion of at least one elipsoid base surface forming a compound elipsoidal surface, said base surface having a major axis and orthogonal minor axes, the major axis, one minor axis and the lateral line lying in a first plane, the other minor axis and the major axis lying in a second plane perpendicular with said first plane, said surface segment being defined as a selected portion of the base surface measured from its origin, said surface segment defined by coordinates corresponding to a displacement of the origin of the base surface to the vicinity of one of a pair of conjugate focci closer to the reflector surface and a rotation of said base surface about said conjugate focus, the rotation of the base surface being accomplished through a selected arc segment about a line perpendicular with the major axis and coplanar with a the second plane for the base surface, each surface segment having lateral boundaries lying in planes converging at acute angles and each including said line about which the segments are rotated.

25. The reflector as described in claim 24 wherein each segment of the base surface is rotated in a direction towards the second plane such that the conjugate focus of each of said segments is shifted away from the said second plane in the vicinity of the limited zone and projections of the illumination from the surface segments to the shifted conjugate focus converge on the major axis at a point beyond the said limited zone.

* * * * *